United States Patent [19]
Steward et al.

[11] 3,980,885
[45] Sept. 14, 1976

[54] DIAGNOSIS BY PROTON BOMBARDMENT

[76] Inventors: Vincent William Steward, 1414 E. 59th St., Apt. No. 753, Chicago, Ill. 60637; Andreas Martin Koehler, 40 Strawberry Hill Road, Concord, Mass. 01742

[22] Filed: Sept. 6, 1974

[21] Appl. No.: 503,619

[52] U.S. Cl. ............................................. 250/307
[51] Int. Cl.² ....................................... G01N 23/00
[58] Field of Search ........... 250/306, 307, 312, 315, 250/315 A, 366, 433

[56] References Cited
UNITED STATES PATENTS

| | | | |
|---|---|---|---|
| 3,370,167 | 2/1968 | Sterk ................................. | 250/306 |
| 3,573,458 | 4/1971 | Anger ................................ | 250/366 |
| 3,761,709 | 9/1973 | Hasegawa et al. ............... | 250/443 X |

OTHER PUBLICATIONS
"Proton Radiography in Tumor Detection" Science, 179(1973), 913–914, Steward et al.

"Observation of Proton Tracks by a Plastic Detector" Varnagy et al, Nuclear Instruments and Methods, 89, No. 1, (1970) pp. 27–28.
"Investigating Crystal Structures with a Proton Beam", Livesey, Electronic Equipment News, vol. 12, No. 8, Nov. 1970, pp. 12–16.

*Primary Examiner*—Davis L. Willis
*Attorney, Agent, or Firm*—Oblon, Fisher, Spivak, McClelland & Maier

[57] ABSTRACT

Beams of monoenergetic protons or other charged ions are passed through the living human body to detect abnormalities and obstructions in body tissue, which abnormalities and obstructions are visualized as density variations in the particle image emerging from the body part under investigation. The particles used are preferably protons having an energy of 100 to 300 MeV, more especially 200 to 300 MeV. The method is of use in detecting inter alia tumors, blood clots, infarcts, soft tissue lesions and multiple sclerosis in patients without exposure to high radiation dosages.

6 Claims, 2 Drawing Figures

DIAGNOSIS BY PROTON BOMBARDMENT

BACKGROUND OF THE INVENTION

1. Field of Invention

The instant invention relates to the use of a proton or other ions beam to detect abnormal density states in the living human body and thereby to diagnose abnormalities or obstructions in living human tissue.

2. Description of Prior Art

X-rays were discovered by Röntgen in 1895 and since then there has been substantial development of X-ray radiography as a diagnostic tool in medicine. However, there are two major drawbacks of using X-rays in medicine; firstly they are exponentially attenuated with sample (i.e. absorber) thickness and secondly their use is hazardous to health. The said second drawback has led to limitations on the use of X-rays for diagnostic purposes. It was suggested by one of us (viz. A. M. Koehler) in a paper entitled "Proton Radiography" (Science, 160 (1968), 303–304) that energetic protons from an accelerator could be used instead of X-rays in both the materials and medical fields because protons are only moderately attenuated with sample thickness before a rapid decrease in flux with increasing thickness towards the end of the particle range. Subsequent papers by Jung (Report GWI — RZ/68, Gustaf Werner Institute, Uppsala, Sweden, 1968); Berger et al (Southwest Research Institute, San Antonio, Texas, 1971 102 – 111); Cookson et al (Non-Destructive Testing, 5 No. 4 (1972), 225–229); and West and Sherwood (Nature, 239 (1972), 157–159) also describe the improvements in contrast obtainable when using protons instead of X-rays.

We have described in our paper entitled "Proton Radiography in Tumor Detection" (Science, 179 (1973), 913–914) how monoenergetic proton beams can be used to provide high contrast radiographs of tumor-bearing human pathologic tissue specimens, in particular brain and breast specimens. using a contact radiography technique. Proton radiography had not, to our knowledge, been used by others prior to 1974 for the investigation of human tissue although proton images of a living rate in which the lungs were clearly visible and in which breathing movements could be observed were obtained by Jung (Report GW1 - RZ/U, supra) and a proton radiograph of a mouse was obtained by West and Sherwood (Nature, supra) using multiple small-angle Coulombe scattering.

SUMMARY OF THE INVENTION

We have now found that monoenergetic proton or other ions beams can be used to distinguish between normal and abnormal density states in the living human body and hence to detect in the body abnormalities or obstructions in the tissue without the risk of cell damage attendant upon the use of X-rays. Said abnormalities or obstructions can be visualized with greater contrast using protons than with X-rays. Moreover, certain abnormalities or obstructions which cannot be visualized with X-rays can be visualized with protons and thus the instant invention can be used to detect blood clots, brain infarcts (i.e. obstructions of brain blood vessels; strokes), multiple sclerosis and heart attacks as well as tumors.

OBJECTS OF THE INVENTION

It is an object of the instant invention therefore to provide a method for distinguishing between normal and abnormal density states in the living human body and hence to detect in the body abnormalities or obstructions in the living tissue.

It is a further object of the instant invention to provide such a method without the risk of cell damage attendant upon the use of X-rays.

It is another object of the instant invention to provide a method of detecting tumors in the living human body.

It is yet another object of the instant invention to provide a method of detecting abnormalities or obstructions within the living human brain.

It is a still further object of the instant invention to provide a method of detecting blood clots and infarcts in the living human brain.

It is another object of the instant invention to provide a method of distinguishing between a blood clot and an infarct in the living human brain.

It is still another object of the present invention to provide a method of detecting soft tissue lesions in the living human body.

It is a still further object of the instant invention to provide a method of detecting multiple sclerosis.

It is yet a further object of the instant invention to provide a method of detecting heart attacks.

Other objects of the instant invention will become apparent from the following description of the preferred embodiments.

DESCRIPTION OF THE PREFERRED EMBODIMENTS

Abnormalities or obstructions in living human tissue are visualized or sought by directing a monoenergetic proton beam through at least part of a living human body and analysing the beam after penetration of the body. Protons at energies of 200 to 300 MeV have sufficient penetrance for investigations on any part of the human body although lower energies can be used for some purposes. At proton kinetic energies above 300 MeV, the attenuation is exponential similar to that of X-rays because of the increased probability of inelastic nuclear collision. Accordingly, at such high kinetic energies, the steeply inclined terminal part of the depth-flux curve and the abrupt terminus in dose seen at lower energies is lost and hence high-contrast radiographs cannot be obtained.

Analysis of the beam after penetration of the body may be based upon particle flux or transmitted energy dependant upon the kind of detection system employed. Generally, radiographic density is believed to be directly related to the flux in film detection systems but transmitted energy is believed to be of important when the detection system is based upon intensifiers or scintillators.

Figure 1:
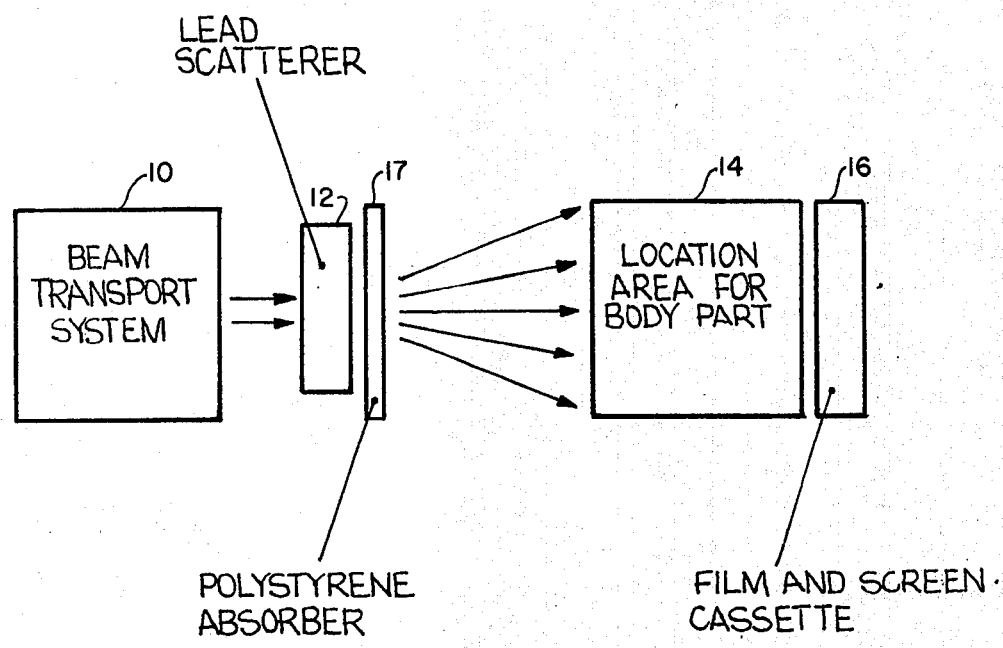
FIG. 1 is a block diagram of apparatus used in accordance with a first embodiment of the invention; and, FIG. 2 is a block diagram of apparatus used in accordance with a second embodiment of the invention.

In most of our investigations, we have used the external 160 MeV proton beam from the Harvard University Cyclotron which, as shown in FIG. 1, has a beam transport system 10 delivering an 0.5 cm diameter focused beam. A broad beam of good uniformity was obtained by diffusing said focused beam by transmission through a lead or copper target or scatterer 12. In this manner, the proton kinetic energy was reduced to about 137 MeV but at a distance of 3 meters the proton flux was substantially uniform to a radius of 10 cm from the beam line. The part of the body having tissue under investigation was therefore located in this region 14. Where possible, such as in tumor investigation of the breast, the area was immersed in water or other tissue-equivalent fluid contained within a plastics box having parallel faces, thereby minimizing the effect of shape irregularities. A photographic film 16 was positioned for the exposure immediately downstream of the plastics box or, in the absence of said box, of the location of the body part in the range of the downward slope of the Bragg Peak of Ionization. It is noted "Bragg Peak" means the peak of the Bragg Curve, which is the graph of the average number of ions per unit distance along the beam of initially monoenergetic ionising particles passing through a gas (source: Chambers Dictionary of Science and Technology, Revised edition, 1974). The energy of the incident protons was adjusted by including thin polystyrene absorbers 17 in the proton path immediately downstream of the target until maximum radiograph contrast was obtained. In this manner it was possible to locate the body part upstream of the Bragg Peak and with the dose throughout the depth of the body part no more than twice the dose at the first surface.

A number of types of photographic film and film-screen combinations were tested for picture quality and sensitivity and Polaroid TLX film with a DuPont HS 1A intensification screen was selected for most of the work. In the high contrast region the said selected combination had a dose reduction factor of about 130 for protons and about 70 for X-rays (used for comparative investigations).

The technique described above can be used to detect the presence of tumors in, for example, the brain or breast (carcinoma); blood clots; infarcts (strokes), multiple sclerosis, heart attacks and other abnormalities or obstructions in living human tissue.

Both primary and secondary brain tumors are well visualized by the technique but not by X-ray radiography even under optimal conditions. Said technique even makes possible visualization of the basal ganglia.

Similarly in stroke patients, the lesions are well visualized with the technique and the major forms can be differentiated from each other.

Blood clots in, for example, subdural haematoma and intracerebral haemorrhage are visualized as areas of greater density than surrounding brain tissue. In contrast, an area damaged by cerebral infarction is visualized as less dense than normal tissue and can be detected in the early case when only comparatively slight changes are apparent on gross inspection. The ability of the method of the instant invention to distinguish between blood clots and infarcts in the living brain is of considerable importance because treatment for the two conditions is totally different and incorrect diagnosis could lead to the patients death.

Breast tumors are visualized as denser areas than normal tissue but unlike the other abnormalities or obstructions specifically referred to herein are also visualizable with X-ray radiography. However, our method provides a high contrast radiograph at a first surface dose significantly lower than that necessary when using conventional X-ray mammographic techniques.

Multiple sclerosis constitutes a destruction of the fatty sheaths which surround nerve fibres and certain brain cells react to the damage by forming scar tissue or plaque which can be visualized by the aforementioned technique.

Instead of using film as the detecting medium, an imaging system can be used to overcome the limited capacity and range of film and to facilitate better spatial resolution. Such a system also permits of image processing and three dimensional imaging. A suitable set-up is shown in FIG. 2.

Figure 2:
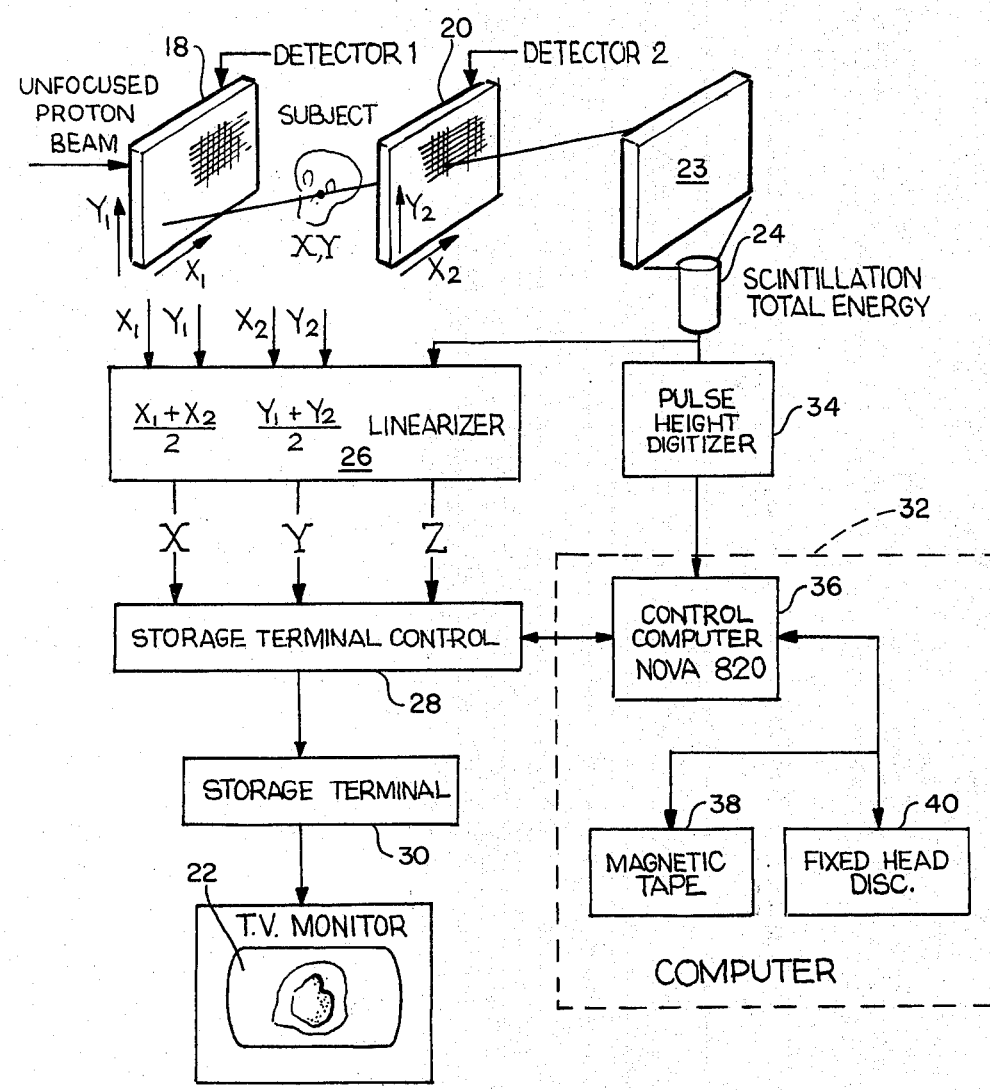

In the set-up of FIG. 2, two detectors 18 and 20 with X and Y co-ordinate read-out are spaced either side of the body part in the proton beam. The detectors can be, for example, spark chambers but multi-wire proportional chambers with at least 0.5mm resolution are preferred to permit of higher event rates up to $10^7$ particles per second. The two detectors have twice the spatial resolution of a single detector and permits of the use of a non-point proton source. The data generated by the detectors is manipulated into a (X,Y) co-ordinate in the body part volume and the information used to deflect a write beam of a silicon storage tube 22 (Hughes Aircraft scan conversion memory tube No. 639) having up to 1,000 line resolution and 100 grey scales storage. The high resolution obtainable with these units can be used to give a zoom capability or to store four independent images. The zoom capability permits of selection of local image regions for detailed analysis and the independent images facility permits of rapid comparison of consecutive exposures.

The intensity is derived from a solid plastics scintillator 23 coupled through a Winston light pipe to a 5 inch diameter photomultiplier 24. A linearizer 26 is used to modulate the signal amplitude from the photomultiplier prior to storage on the silicon storage tube target.

The data flow to the storage terminal control 28 and storage terminal 30 bypasses the computer 32 in the set-up of FIG. 2 but digital information from the detector can be transferred from a pulse height digitizer 34 to the control computer 36 for storage on a magnetic tape 38 or a magnetic disk 40. In an alternative mode, the data on the storage tube is integrated and a permanent record made by reading data off the tube and digitizing.

Recent work has been conducted using a beam of 200 MeV monoenergetic protons from the 12 GeV Gradient Synchrotron (ZGS) of the Argonne National Laboratories. Scanning methods are being developed with this beam to provide by way of two collinator systems an array of 20–40 1mm beams to scan a patient in a very short time.

Other particularly useful charged particles for use in the method of the instant invention are deuterium and tritium ions.

The method of the instant invention usually involves exposure of the living human body to a first surface dose of less than 1 rad, typically 0.3 rad using the film technique described above with reference to FIG. 2. With an imaging system such as that described with reference to FIG. 2, the first surface dose level can reasonably be predicted to be within the range 1 to 0.1 millirad of most investigations of the human body. In comparison, a normal background exposure at sea level is 100 millirads per year. Hence the method of our invention will permit of screening those at risk as well as those who are ill without fear of harm which is attendant upon the use of X-rays.

The following Examples are given to illustrate the instant invention by way of specific embodiments but are not intended to impose any limitation upon the scope of the invention claimed.

EXAMPLE 1.

In the set-up of FIG. 1, the plastic box was located immediately below a hole in a support table for the patient and filled with water so that one breast of a female patient laying face down on said table protruded into the water. The table was located so that the proton beam from the Harvard Cyclotron after passage through the target and polystyrene absorber as described above passed horizontally and transversely through the breast in the water before the Bragg Peak. A Polaroid TLX radiograhpic film packet with a DuPont HS IA intensification screen was located downstream of and immediately adjacent to the water box in a position within the region of downward slope of the Bragg Peak. Female patients having suspected carcinoma of the breast were laid in position in the table with the breast to be examined protruding into the water box and subjected to a short exposure to the proton beam so that the first surface dose was slightly less than 0.3 rad. The film was developed and the image studied to detect tumors as dark areas of the image.

In one particular case, a 43-year old black woman had noticed an itchy small lump over the left nipple some three years before examination. The lump grew to a fungating, bleeding lesion of approximately 8cm diameter. Several small, firm skin metastases were present medial to the main lesion and large lymph nodes were palpable within the left axilla. Proton radiography as above showed a dark dense area corresponding to the side of the lump with greater contrast than possible with conventional X-ray techniques and at a much lower radiation level.

EXAMPLE 2

Using the set-up of FIG. 1, a human skull containing a brain was located in the water box located upstream of the Bragg Peak and Polaroid TLX film with a Radelin TF intensification screen was located downstream of and immediately adjacent to the water box in a position within the downwardly sloping region of the Bragg Peak. The brain in the skull was a tumor-bearing brain hemisphere which had previously been examined in the same set-up but outside a skull (see our Science paper supra). After exposure of the brain-containing skull to the proton beam for an estimated first surface dose of slightly less than 0.5 rad, the film was developed and the image studied. The tumor could clearly be seen on the image as an area of greater density. As far as we are aware, this was the first time that a non-calcified brain tumor had been visualized in a state equivalent to the living intact human head. In the case of living brain examination, it is necessary to exclude the water box and hence some loss of contrast is seen; nevertheless the tumor would still be visualized on the image.

Similar exposure of the living brain, heart, lungs, liver and other soft tissues provides visualization of abnormalities and obstructions in those tissues such as, for example, cerebral haemorrhage and infarction (strokes), myocardial infarction (heart attack), pulmonary oedema, multiple sclerosis and cirrhosis.

It will be appreciated that the invention is not restricted to the particular description given above. Obviously, many modifications and variations of the instant invention are possible in the light of the teachings above.

What is claimed is:

1. A new use for charged ion particle beams in the field of diagnostic radiology comprising the steps of:
    selecting a region of the living human body for radiological study,
    producing a monoenergetic charged ion particle beam, said beam exhibiting a peak in ionization towards the end of the charged ion particle range in the average number of ion particles produced per unit distance along the beam,
    locating said region of the living human body upstream of the position of the peak in the average number of ion particles produced per unit distance along said monoenergetic charged ion particle beam,
    passing said monoenergetic charged ion particle beam through said region of said living human body,
    producing an image of said monoenergetic charged ion beam subsequent to its passage through said region of said living human body; and
    diagnosing abnormal conditions in said region of said living human body in reliance upon said image.

2. A new use for charged ion particle beams as in claim 1, wherein:
    said step of beam producing includes the step of generating a beam of monoenergetic protons having an energy between 100 and 300 MeV.

3. A new use for charged ion particle beams as in claim 2, wherein:
    said step of image producing includes the step of forming an image which distinguishes between normal and adnormal density states in the human body.

4. A new use for charged ion particle beams as in claim 1, wherein:
    said step of selecting includes the step of choosing the human brain as said region,
    said step of image producing includes the step of forming an image of density variations within the human brain; and,
    said step of diagnosing includes the step of distinguishing between blood clots and infarcts in reliance upon said image.

5. A new use for charged ion particle beams as in claim 1, wherein:
    said step of selecting includes the step of choosing the human head as said region,
    said step of image producing includes the step of forming an image of density variations within the human head; and,
    said step of diagnosing includes the step of detecting multiple sclerosis in reliance upon said image.

6. A new use for charged ion particle beams as in claim 1, wherein:
    said step of selecting includes the step of choosing the human heart as said region,
    said step of image producing includes the step of forming an image of density variations within the human heart; and,
    said step of diagnosing includes the step of detecting heart attacks in reliance upon said image.

* * * * *